US010881377B2

(12) United States Patent
Ebrahimi et al.

(10) Patent No.: US 10,881,377 B2
(45) Date of Patent: Jan. 5, 2021

(54) SINUS DILATION CATHETER WITH ULTRASONIC IMAGING FEATURE

(71) Applicant: Acclarent, Inc., Irvine, CA (US)

(72) Inventors: Babak Ebrahimi, Irvine, CA (US); Don Q. Ngo-Chu, Irvine, CA (US); Jetmir Palushi, Irvine, CA (US); Ehsan Shameli, Irvine, CA (US)

(73) Assignee: Acclarent, Inc., Irvine, CA (US)

( * ) Notice: Subject to any disclaimer, the term of this patent is extended or adjusted under 35 U.S.C. 154(b) by 96 days.

(21) Appl. No.: 15/832,143

(22) Filed: Dec. 5, 2017

(65) Prior Publication Data
US 2019/0167228 A1    Jun. 6, 2019

(51) Int. Cl.
*A61B 8/00* (2006.01)
*A61M 25/00* (2006.01)
(Continued)

(52) U.S. Cl.
CPC ............ *A61B 8/445* (2013.01); *A61B 8/12* (2013.01); *A61B 8/4281* (2013.01); *A61B 17/24* (2013.01);
(Continued)

(58) Field of Classification Search
CPC ......... A61B 8/445; A61B 8/12; A61B 8/4281; A61B 8/44; A61B 17/24; A61B 2090/378; A61B 2090/3784; A61B 1/00082; A61B 1/00133; A61B 1/00147; A61B 5/065; A61B 5/066; A61B 5/6819; A61M 25/0108; A61M 25/0158; A61M 2205/07; A61M 25/0113; A61M 25/09041;
(Continued)

(56) References Cited

U.S. PATENT DOCUMENTS 4,841,977 A * 6/1989 Griffith .................... A61B 8/12
                                                        29/25.35
5,040,548 A * 8/1991 Yock .................... A61B 18/245
                                                        128/898
(Continued)

OTHER PUBLICATIONS

Rothman, Abraham, et al. "Intraluminal ultrasound imaging through a balloon dilation catheter in an animal model of coarctation of the aorta." *Circulation* 85.6 (1992): 2291-2295.
(Continued)

*Primary Examiner* — Nilay J Shah
(74) *Attorney, Agent, or Firm* — Frost Brown Todd LLC

(57) ABSTRACT

A dilation instrument and method of imaging an anatomy within a patient includes a dilation catheter having a catheter body, a fluid conduit extending along the catheter body, a dilator, and at least one ultrasonic transducer. The catheter body is configured to distally extend from an instrument body and move relative to the instrument body. The dilator is connected to the catheter body in fluid communication with the fluid conduit and configured to receive a fluid from the fluid conduit and thereby inflate from a contracted state to an expanded state. The at least one ultrasonic transducer positioned on the catheter body and configured to electrically connect to an ultrasonic generator. The at least one ultrasonic transducer is configured to emit a source ultrasonic signal toward an anatomy within a patient for producing a diagnostic or a therapeutic effect.

20 Claims, 7 Drawing Sheets

(51) Int. Cl.
*A61B 8/12* (2006.01)
*A61B 17/24* (2006.01)
*A61M 25/02* (2006.01)
*A61M 29/02* (2006.01)
*A61M 25/01* (2006.01)
*A61B 90/00* (2016.01)
*A61B 1/00* (2006.01)
*A61B 1/01* (2006.01)
*A61N 7/00* (2006.01)
*A61M 25/09* (2006.01)

(52) U.S. Cl.
CPC ....... *A61M 25/005* (2013.01); *A61B 1/00082* (2013.01); *A61B 1/00133* (2013.01); *A61B 1/00147* (2013.01); *A61B 1/01* (2013.01); *A61B 2090/3784* (2016.02); *A61M 25/0108* (2013.01); *A61M 25/0113* (2013.01); *A61M 25/0158* (2013.01); *A61M 25/09041* (2013.01); *A61M 29/02* (2013.01); *A61M 2025/0226* (2013.01); *A61N 2007/0043* (2013.01); *A61N 2007/0052* (2013.01); *A61N 2007/0095* (2013.01)

(58) Field of Classification Search
CPC .... A61N 2007/0043; A61N 2007/0052; A61N 2007/0095
See application file for complete search history.

(56) References Cited

U.S. PATENT DOCUMENTS

| | | | | |
|---|---|---|---|---|
| 5,137,288 | A | * | 8/1992 | Starkey ................ A61M 25/09 279/42 |
| 5,458,568 | A | * | 10/1995 | Racchini ............ A61M 25/104 604/103.01 |
| 5,846,205 | A | * | 12/1998 | Curley ................. A61B 1/0052 600/472 |
| 6,296,619 | B1 | * | 10/2001 | Brisken .............. A61B 17/2202 600/466 |
| 6,334,846 | B1 | * | 1/2002 | Ishibashi ............ A61B 17/2256 600/412 |
| 9,155,492 | B2 | | 10/2015 | Jenkins et al. |
| 2008/0183128 | A1 | | 7/2008 | Morriss et al. |
| 2009/0024034 | A1 | * | 1/2009 | Moreau-Gobard .......................... A61B 8/4227 600/443 |
| 2009/0228003 | A1 | | 9/2009 | Sinelnikov |
| 2010/0030031 | A1 | | 2/2010 | Goldfarb et al. |
| 2010/0204561 | A1 | | 8/2010 | Saadat et al. |
| 2011/0004057 | A1 | | 1/2011 | Goldfarb et al. |
| 2011/0251492 | A1 | * | 10/2011 | Forster ................ A61B 5/0066 600/470 |
| 2012/0071857 | A1 | * | 3/2012 | Goldfarb ............... A61B 17/24 604/514 |
| 2012/0095334 | A1 | | 4/2012 | Forster et al. |
| 2012/0259263 | A1 | | 10/2012 | Celermajor et al. |
| 2014/0074141 | A1 | | 3/2014 | Johnson et al. |
| 2015/0165244 | A1 | | 6/2015 | Kardosh et al. |
| 2016/0310714 | A1 | | 10/2016 | Jenkins et al. |
| 2017/0021148 | A9 | | 1/2017 | Deem et al. |
| 2017/0120020 | A1 | | 5/2017 | Lin et al. |

OTHER PUBLICATIONS

International Search Report and Written Opinion dated Jun. 13, 2019 for International Application No. PCT/IB2019/059639, 21 pages.

* cited by examiner

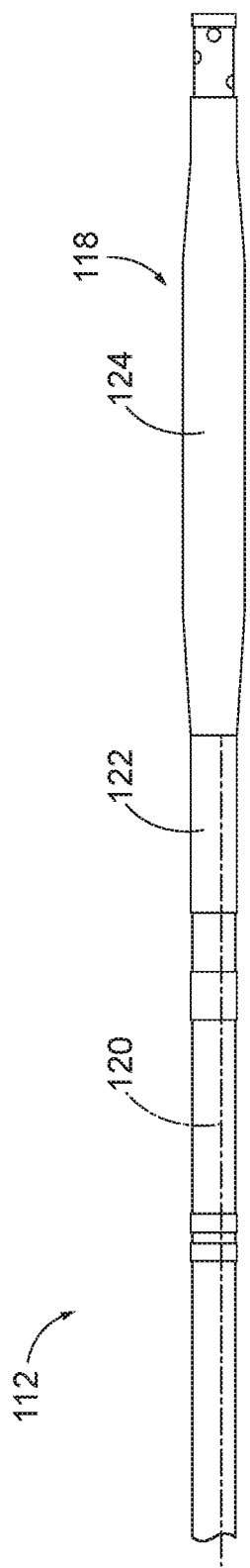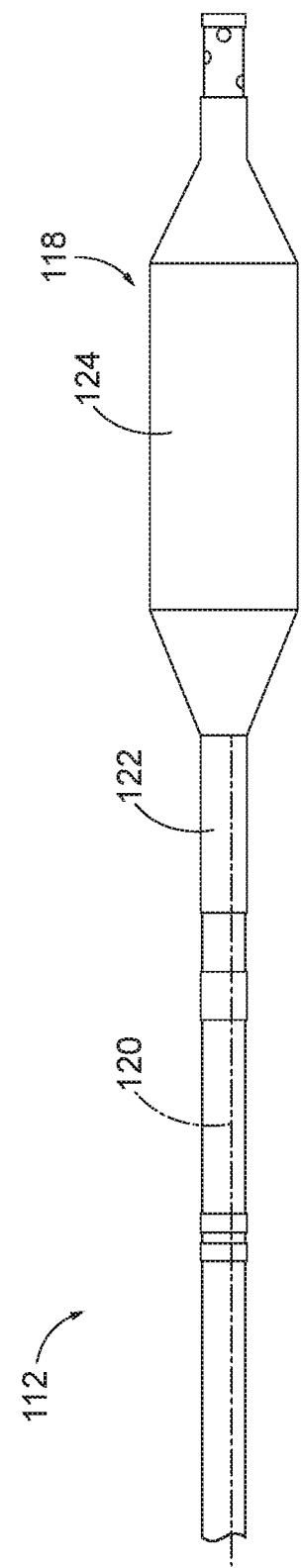
FIG. 3A
FIG. 3B

SINUS DILATION CATHETER WITH ULTRASONIC IMAGING FEATURE

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guidewire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Irvine, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, now abandoned, the disclosure of which is incorporated by reference herein.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pat. No. 9,155,492, entitled "Sinus Illumination Lightwire Device," issued Oct. 13, 2015, the disclosure of which is incorporated by reference herein. An example of such an illuminating guidewire is the Relieva Luma Sentry™ Sinus Illumination System by Acclarent, Inc. of Irvine, Calif.

Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.) so as to superimpose the current location of the instrument on the preoperatively obtained images. In some IGS procedures, a digital tomographic scan (e.g., CT or MRI, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) mounted thereon are used to perform the procedure while the sensors send data to the computer indicating the current position of each surgical instrument. The computer correlates the data it receives from the instrument-mounted sensors with the digital map that was created from the preoperative tomographic scan. The tomographic scan images are displayed on a video monitor along with an indicator (e.g., cross hairs or an illuminated dot, etc.) showing the real time position of each surgical instrument relative to the anatomical structures shown in the scan images. In this manner, the surgeon is able to know the precise position of each sensor-equipped instrument by viewing the video monitor even if the surgeon is unable to directly visualize the instrument itself at its current location within the body.

Examples of electromagnetic IGS systems that may be used in ENT and sinus surgery include the Intertek ENT™ systems available from GE Medical Systems, Salt Lake City, Utah. Other examples of electromagnetic image guidance systems that may be modified for use in accordance with the present disclosure include but are not limited to the CARTO® 3 System by Bio sense-Webster, Inc., of Irvine, Calif.; systems available from Surgical Navigation Technologies, Inc., of Louisville, Colo.; and systems available from Calypso Medical Technologies, Inc., of Seattle, Wash.

When applied to functional endoscopic sinus surgery (FESS), balloon sinuplasty, and/or other ENT procedures, the use of image guidance systems allows the surgeon to achieve more precise movement and positioning of the surgical instruments than can be achieved by viewing through an endoscope alone. This is so because a typical endoscopic image is a spatially limited, 2-dimensional, line-of-sight view. The use of image guidance systems provides a real time, 3-dimensional view of all of the anatomy surrounding the operative field, not just that which is actually visible in the spatially limited, 2-dimensional, direct line-of-sight endoscopic view. As a result, image guidance systems may be particularly useful during performance of FESS, balloon sinuplasty, and/or other ENT procedures where a section and/or irrigation source may be desirable, especially in cases where normal anatomical landmarks are not present or are difficult to visualize endoscopically.

While several systems and methods have been made and used in ENT procedures, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 3A depicts a side elevational view of a distal end portion of the dilation catheter of FIG. 2 with a dilator in a contracted state;

FIG. 3B depicts the side elevational view of the distal end portion of the dilation catheter similar to FIG. 3A, but with the dilator in an expanded state;

Figure 1A:
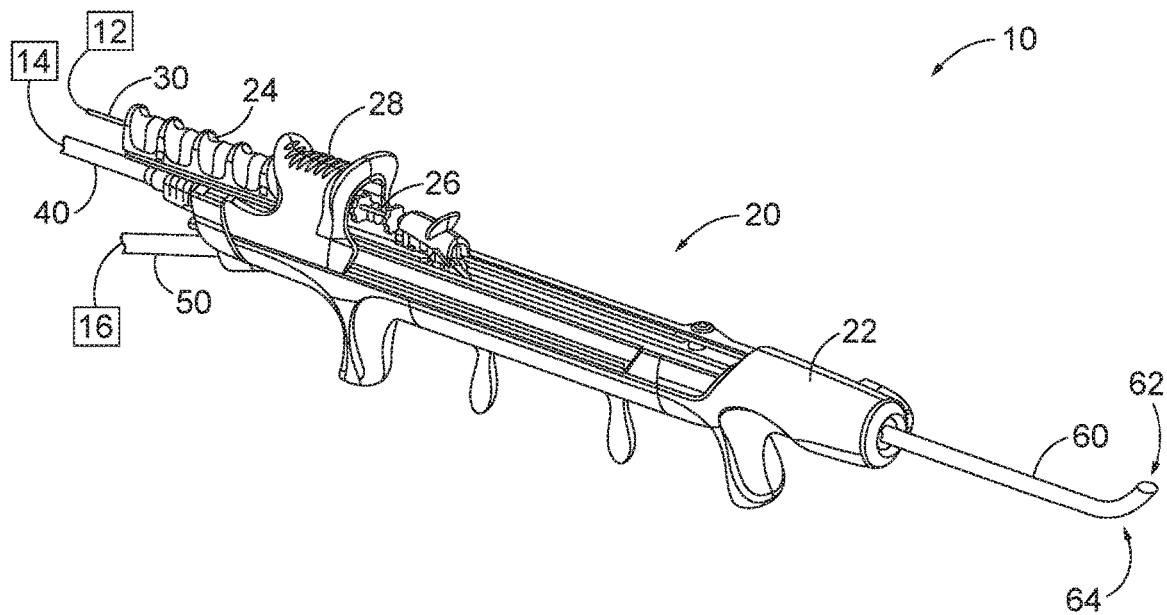
FIG. 1A depicts a perspective view of an exemplary dilation instrument assembly, with an exemplary guidewire in a proximal position, and with a first exemplary dilation catheter in a proximal position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Dilation Catheter System

FIGS. 1A-1D shows a first exemplary dilation instrument assembly (10) that may be used to dilate the ostium of a paranasal sinus; to dilate some other passageway associated with drainage of a paranasal sinus; to dilate a Eustachian tube; or to dilate some other anatomical passageway (e.g., within the ear, nose, or throat, etc.). Dilation instrument assembly (10) of this example comprises a guidewire power source (12), an inflation source (14), an irrigation fluid source (16), and a dilation instrument (20). In some versions, guidewire power source (12) is part of an IGS system as described below with respect to FIGS. 2-3. In some other versions, guidewire power source (12) comprises a source of light as described below with respect to FIGS. 4-6. In the present example shown in FIGS. 1A-1D, inflation source (14) comprises a source of saline. However, it should be understood that any other suitable source of fluid (liquid or otherwise) may be used. Also in the present example, irrigation fluid source (16) comprises a source of saline. Again, though, any other suitable source of fluid may be used. It should also be understood that flush fluid source (16) may be omitted in some versions.

Dilation instrument (20) of the present example comprise a handle body (22) with a guidewire slider (24), a guidewire spinner (26), and a dilation catheter slider (28). Handle body (22) is sized and configured to be gripped by a single hand of a human operator. Sliders (24, 28) and spinner (26) are also positioned and configured to be manipulated by the same hand that grasps handle body (22). It should therefore be understood that dilation instrument (20) may be fully operated by a single hand of a human operator.

A. Exemplary Guide Catheter

A guide catheter (60) extends distally from handle body (22). Guide catheter (60) includes an open distal end (62) and a bend (64) formed proximal to open distal end (62). In the present example, dilation instrument (20) is configured to removably receive several different kinds of guide catheters (60), each guide catheter (60) having a different angle formed by bend (64). These different angles may facilitate access to different anatomical structures. Various examples of angles and associated anatomical structures are described in one or more of the references cited herein; while further examples will be apparent to those of ordinary skill in the art in view of the teachings herein. Guide catheter (60) of the present example is formed of a rigid material (e.g., rigid metal and/or rigid plastic, etc.), such that guide catheter (60) maintains a consistent configuration of bend (64) during use of dilation instrument (20). In some versions, dilation instrument (20), is further configured to enable rotation of guide catheter (60), relative to handle body (22), about the longitudinal axis of the straight proximal portion of guide catheter (60), thereby further promoting access to various anatomical structures.

B. Exemplary Guidewire

Figure 1B:
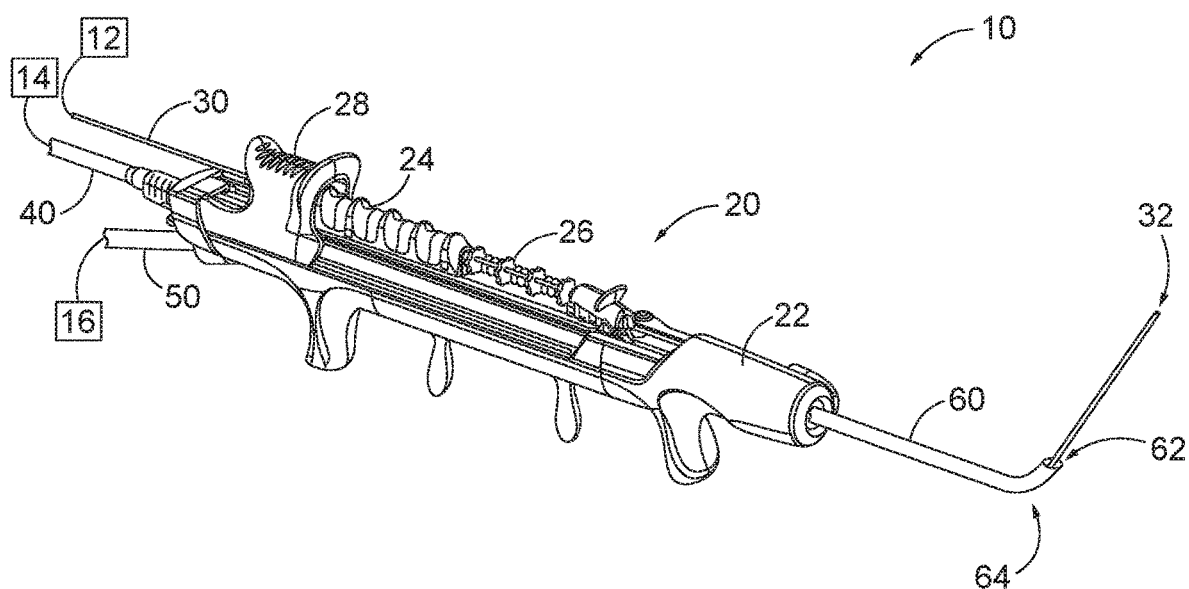
FIG. 1B depicts a perspective view of the dilation instrument assembly of FIG. 1A, with the guidewire in a distal position, and with the dilation catheter in the proximal position.

Dilation instrument (20) further comprises an exemplary guidewire (30), which is coaxially disposed in guide catheter (60). Guidewire slider (24) is secured to guidewire (30) such that translation of guidewire slider (24) relative to handle body (22) provides corresponding translation of guidewire (30) relative to handle body (22). In particular, translation of guidewire slider (24) from a proximal position (FIG. 1A) to a distal position (FIG. 1B) causes corresponding translation of guidewire (30) from a proximal position (FIG. 1A) to a distal position (FIG. 1B). When guidewire (30) is in a distal position, a distal portion of guidewire (30) protrudes distally from open distal end (62) of guide catheter (60). Guidewire spinner (26) is operable to rotate guidewire (30) about the longitudinal axis of guidewire (30). Guidewire spinner (26) is coupled with guidewire slider (24) such that guidewire spinner (26) translates longitudinally with guidewire slider (24).

In some versions, guidewire (30) includes a preformed bend formed just proximal to a distal end (32) of guidewire (30). In such versions, the preformed bend and the rotatability provided via guidewire spinner (26) may facilitate alignment and insertion of distal end (32) into a sinus ostium, Eustachian tube, or other passageway to be dilated. Also in some versions, guidewire (30) includes at least one optical fiber extending to a lens or other optically transmissive feature in distal end (32), such as illuminating guidewire (150) (see FIGS. 4-6) discussed below. Optical fiber may be in optical communication with guidewire power source (12), such that light may be communicated from guidewire power source (12) to distal end (32). In such versions, guidewire (30) may provide transillumination through a patient's skin in order to provide visual feedback to the operator indicating that distal end (32) has reached a targeted anatomical structure.

By way of example only, guidewire (30) may be configured in accordance with at least some of the teachings of U.S. Pat. No. 9,155,492, the disclosure of which is incorporated by reference herein. In some versions, guidewire (30) is configured similar to the Relieva Luma Sentry™ Sinus Illumination System by Acclarent, Inc. of Irvine, Calif. In addition to, or as an alternative to, including one or more optical fibers, guidewire (30) may include a sensor and at least one wire that enables guidewire (30) to provide compatibility with an IGS system as described in greater detail below. Other features and operabilities that may be incorporated into guidewire (30) will be apparent to those of ordinary skill in the art in view of the teachings herein.

C. Exemplary Dilation Catheter

Figure 1C:
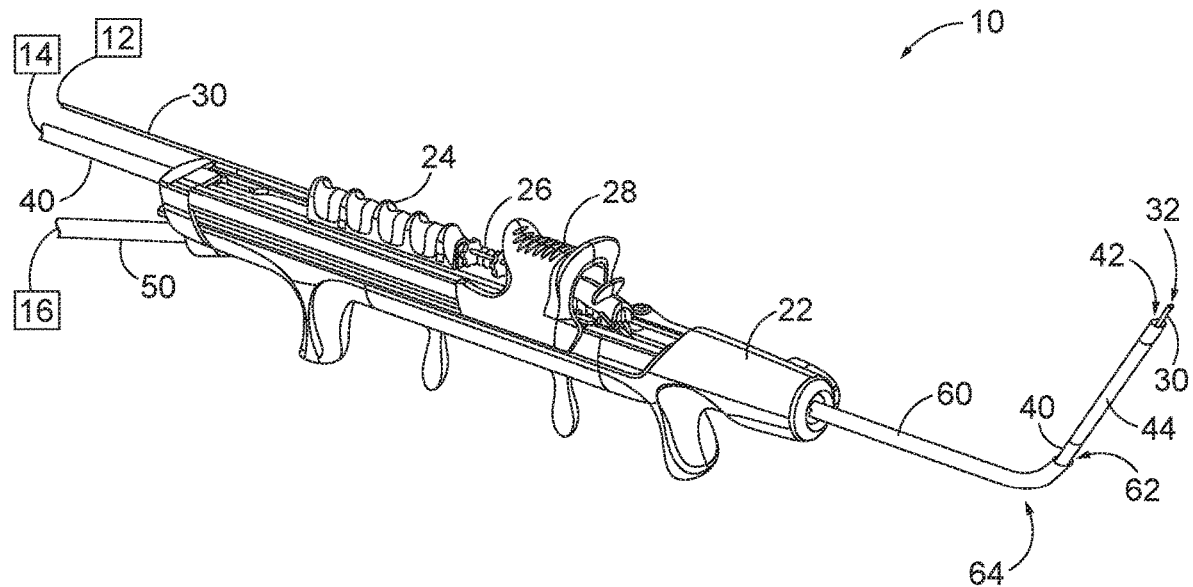
FIG. 1C depicts a perspective view of the dilation instrument assembly of FIG. 1A, with the guidewire in a distal position, with the dilation catheter in a distal position, and with a dilator of the dilation catheter in a non-dilated state.

Dilation instrument (20) further comprises a first exemplary dilation catheter (40), which is coaxially disposed in guide catheter (60). Dilation catheter slider (28) is secured to dilation catheter (40) such that translation of dilation catheter slider (28) relative to handle body (22) provides corresponding translation of dilation catheter (40) relative to handle body (22). In particular, translation of dilation catheter slider (28) from a proximal position (FIG. 1B) to a distal position (FIG. 1C) causes corresponding translation of dilation catheter (40) from a proximal position (FIG. 1B) to a distal position (FIG. 1C). When dilation catheter (40) is in a distal position, a distal portion of dilation catheter (40) protrudes distally from open distal end (62) of guide catheter (60). As can also be seen in FIG. 1C, a distal portion of guidewire (30) protrudes distally from the open distal end of dilation catheter (40) when guidewire (30) and dilation catheter are both in distal positions.

Figure 1D:
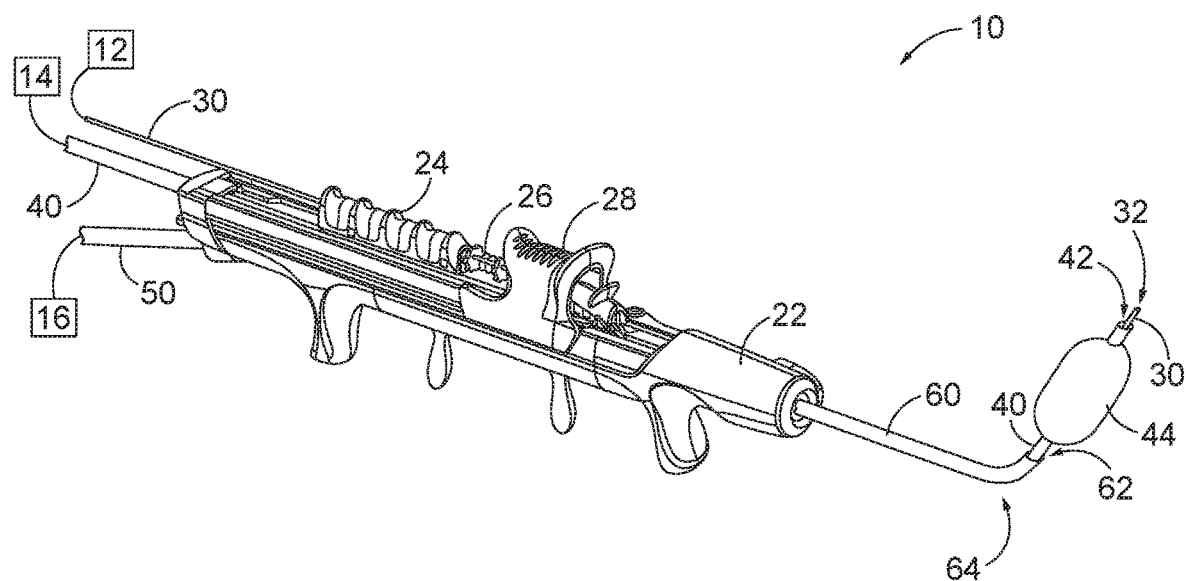
FIG. 1D depicts a perspective view of the dilation instrument assembly of FIG. 1A, with the guidewire in a distal position, with the dilation catheter in the distal position, and with a dilator of the dilation catheter in a dilated state.

Dilation catheter (40) of the present example comprises a non-extensible balloon (44) located just proximal to an open distal end (42) of dilation catheter (40). Balloon (44) is in fluid communication with inflation source (14). Inflation source (14) is configured to communicate fluid (e.g., saline, etc.) to and from balloon (44) to thereby transition balloon (44) between a non-inflated state and an inflated state. FIG. 1C shows balloon (44) in a contracted, non-inflated state. FIG. 1D shows balloon (44) in an expanded, inflated state. In some versions, inflation source (14) comprises a manually actuated source of pressurized fluid. In some such versions, the manually actuated source of pressurized fluid is configured and operable in accordance with at least some of the teachings of U.S. Pub. No. 2014/0074141, entitled "Inflator for Dilation of Anatomical Passageway," published Mar. 13, 2014, issued as U.S. Pat. No. 9,962,530 on May 8, 2018, the disclosure of which is incorporated by reference herein. Other suitable configurations that may be used to provide a source of pressurized fluid will be apparent to those of ordinary skill in the art in view of the teachings herein.

While not shown, it should be understood that dilation catheter (40) may include at least two separate lumens that are in fluid isolation relative to each other. One lumen may provide a path for fluid communication between balloon (44) and inflation source (14). The other lumen may provide a path to slidably receive guidewire (30).

While dilation catheter (40) of the present example is configured to transition between a non-dilated state and a dilated state based on the communication of fluid to and from balloon (44), it should be understood that dilation catheter (40) may include various other kinds of structures to serve as a dilator. By way of example only, balloon (44) may be replaced with a mechanical dilator in some other versions. Dilation catheter (40) may be constructed and operable in accordance with any of the various references cited herein. In some versions, dilator catheter (40) is configured and operable similar to the Relieva Ultirra™ Sinus Balloon Catheter by Acclarent, Inc. of Irvine, Calif. In some other versions, dilator catheter (40) is configured and operable similar to the Relieva Solo Pro™ Sinus Balloon Catheter by Acclarent, Inc. of Irvine, Calif. Other suitable variations of dilation catheter (40) will be apparent to those of ordinary skill in the art in view of the teachings herein.

D. Exemplary Irrigation Features

In some instances, it may be desirable to irrigate an anatomical site. For instance, it may be desirable to irrigate a paranasal sinus and nasal cavity after dilation catheter (40) has been used to dilate an ostium or other drainage passageway associated with the paranasal sinus. Such irrigation may be performed to flush out blood, etc. that may be present after the dilation procedure. In some such cases, guide catheter (60) may be allowed to remain in the patient while guidewire (30) and dilation catheter (40) are removed. A dedicated irrigation catheter (not shown) may then be inserted into guide catheter (60) and coupled with irrigation fluid source (16) via tube (50), to enable irrigation of the anatomical site in the patient. An example of an irrigation catheter that may be fed through guide catheter (60) to reach the irrigation site after removal of dilation catheter (60) is the Relieva Vortex® Sinus Irrigation Catheter by Acclarent, Inc. of Irvine, Calif. Another example of an irrigation catheter that may be fed through guide catheter (60) to reach the irrigation site after removal of dilation catheter (40) is the Relieva Ultirra® Sinus Irrigation Catheter by Acclarent, Inc. of Irvine, Calif.

In some other versions, dilation catheter (40) includes an additional irrigation lumen and an associated set of irrigation ports near distal end (42), such that dilation catheter (40) may be coupled with irrigation fluid source (16) via tube (50). Thus, a separate, dedicated irrigation catheter is not necessarily required in order to provide irrigation.

By way of example only, irrigation may be carried out in accordance with at least some of the teachings of U.S. Pub. No. 2008/0183128, entitled "Methods, Devices and Systems for Treatment and/or Diagnosis of Disorders of the Ear, Nose and Throat," published on Jul. 31, 2008, now abandoned, the disclosure of which is incorporated by reference herein. Of course, irrigation may be provided in the absence of a dilation procedure; and a dilation procedure may be completed without also including irrigation. It should therefore be understood that dilation fluid source (16) and tube (50) are merely optional.

E. Exemplary Variations

In the present example, guidewire (30) is coaxially disposed within dilation catheter (40), which is coaxially disposed within guide catheter (60). In some other versions, guide catheter (60) is omitted from dilation instrument (20). In some such versions, a malleable guide member is used to guide guidewire (30) and dilation catheter (40). In some such versions, guidewire (30) is omitted and dilation catheter (40) is slidably disposed about the exterior of the internal malleable guide member. In some other versions, guidewire (30) is slidably disposed about the exterior of the internal malleable guide member; and dilation catheter (40) is slidably disposed about the exterior of guidewire (30). In still other versions, guidewire (30) is slidably disposed within the interior of the malleable guide member; and dilation catheter (40) is slidably disposed about the exterior of the malleable guide member.

By way of example only, versions of dilation instrument (20) that include a malleable guide member may be constructed and operable in accordance with at least some of the teachings of U.S. Pub. No. 2016/0310714, entitled "Balloon Dilation System with Malleable Internal Guide," published Oct. 27, 2016, issued as U.S. Pat. No. 10,137,285 on Nov. 27, 2018, the disclosure of which is incorporated by reference herein. As another merely illustrative example, versions of dilation instrument (20) that include a malleable guide member may be constructed and operable in accordance with at least some of the teachings of U.S. patent application Ser. No. 14/928,260, entitled "Apparatus for Bending Malleable Guide of Surgical Instrument," filed Oct. 30, 2015, issued as U.S. Pat. No. 10,137,286 on Nov. 27, 2018, the disclosure of which is incorporated by reference herein; and/or U.S. Pub. No. 2012/0071857, entitled "Methods and Apparatus for Treating Disorders of the Sinuses," published Mar. 22, 2012, now abandoned, the disclosure of which is incorporated by reference herein.

It should be understood that the variations of dilation instrument (20) described below in the context of an IGS system may be incorporated into versions of dilation instrument (20) having a malleable guide just like the variations of dilation instrument (20) described below in the context of an IGS system may be incorporated into versions of dilation instrument (20) having a rigid guide catheter (60).

Various examples below describe the use of an IGS system to provide navigation of instruments within a patient. In particular, various examples below describe how dilation instrument assembly (10) may be modified to incorporate IGS system features. However, it should also be understood that dilation instrument assembly (10) may be used in conjunction with conventional image guidance instruments, in addition to being used with IGS system components. For instance, dilation instrument assembly (10) may be used in conjunction with an endoscope, at least to provide initial positioning of guide catheter (60) in a patient. By way of example only, such an endoscope may be configured in accordance with at least some of the teachings of U.S. Pub. No. 2010/0030031, now abandoned, the disclosure of which is incorporated by reference herein. Other suitable kinds of endoscopes that may be used with the various versions of dilation instrument assembly (10) described herein will be apparent to those of ordinary skill in the art.

II. Ultrasonic Imaging System

Figure 2:
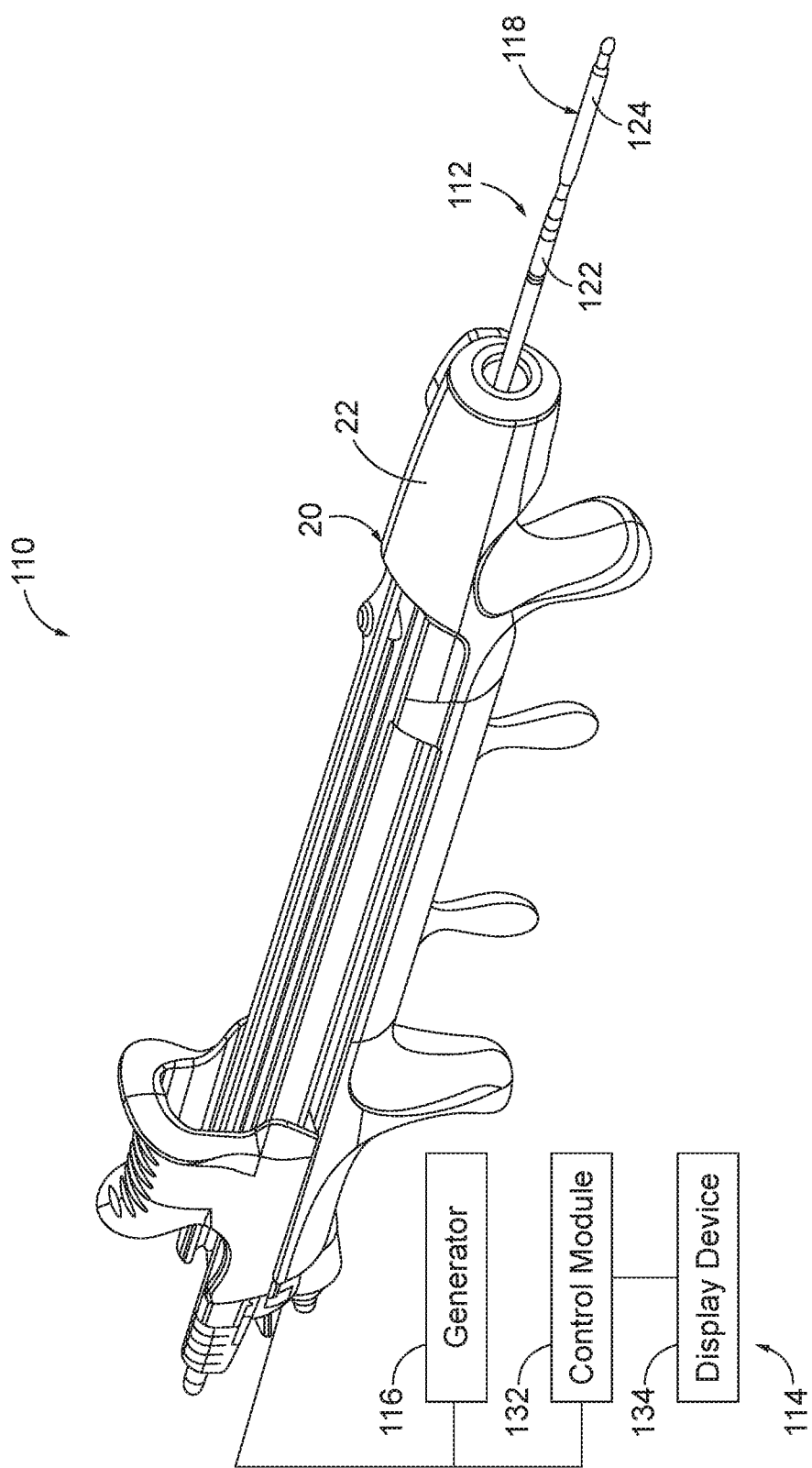
FIG. 2 depicts a perspective view of another exemplary dilation instrument assembly with a second exemplary dilation catheter and an ultrasonic imaging system as well as various components removed for clarity.

FIG. 2 shows another exemplary dilation instrument assembly (110) including dilation instrument (20), guidewire (30) (see FIG. 1B), and guide catheter (60) as discussed above in addition to a second exemplary dilation catheter (112) with an ultrasonic imaging system (114). Dilation instrument (20), guidewire (30) (see FIG. 1B), and guide catheter (60) operate generally as discussed above such that like numbers indicate like features. Dilation catheter (112) also operates similar to dilation catheter (40), but, in addition, interfaces with ultrasonic imaging system (114) for imaging an anatomy within a patient. Imaging may be useful feedback to produce a therapeutic effect or a diagnostic effect for enhanced patient outcomes. Such therapeutic effects include, but are not limited to, directing dilation instrument assembly (110) according to a predetermined response or directing clinician to manipulate dilation instrument assembly (110) according to the predetermined response. In contrast, diagnostic effects include, but are not limited to, communicating data, such as by visual representation, regarding the anatomy within the patient so that the clinician may more effectively diagnose and treat the patient.

With respect to FIGS. 2-3B, ultrasonic imaging system (114) includes an ultrasonic generator (116) electrically connected to an imaging dilator (118), such as via electrical wiring (not shown). A fluid conduit (120) extends along a catheter body (122) of dilation catheter (112) with a proximal opening in fluid communication with inflation source (14) (see FIG. 1A) and a distal opening in fluid communication with imaging dilator (118). Without fluid, imaging dilator remains in the non-inflated, contracted state shown in FIG. 3A. However, directing fluid distally along fluid conduit (120) and into imaging dilator (118) expands imaging dilator (118) to the inflated, expanded state shown in FIG. 3B.

Figure 4:
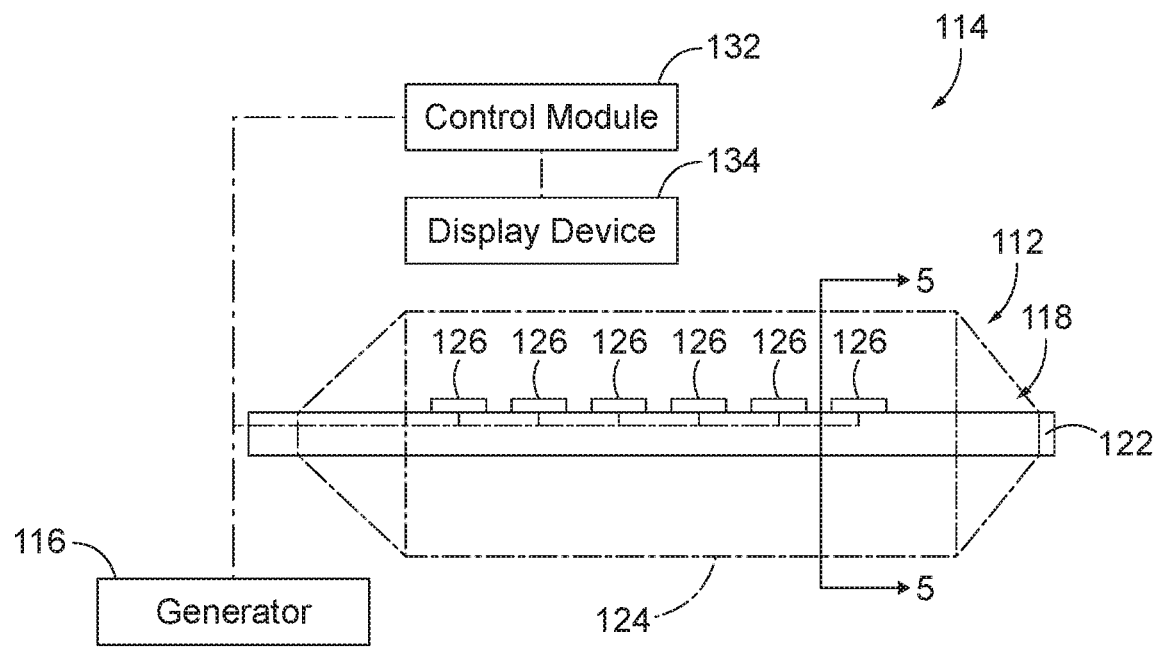
FIG. 4 depicts an enlarged side elevational view of the distal end portion of the dilation catheter of FIG. 3B having various components hidden for more clearly showing a plurality of electrically reactive components of the ultrasonic imaging system.
Figure 5:
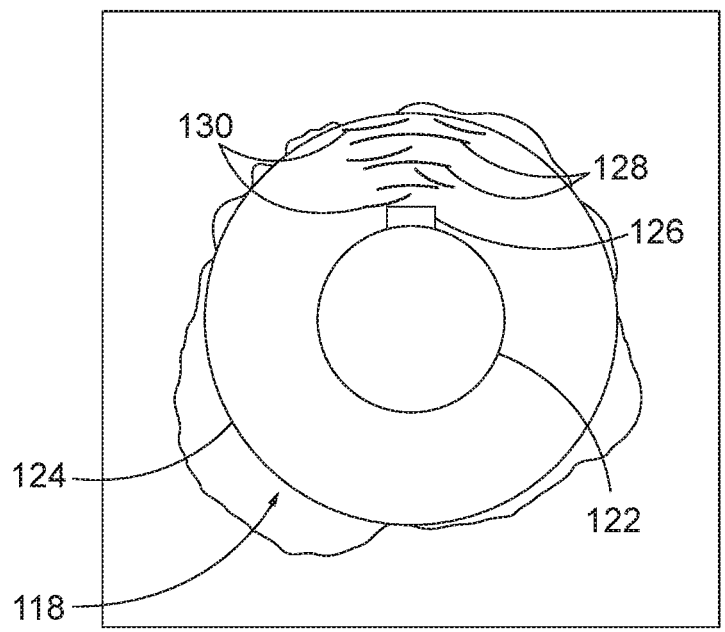
FIG. 5 depicts a cross-sectional view of the dilation catheter taken along section line 5-5 of FIG. 4 in the expanded state and within an anatomy to generate an image of the anatomy with the ultrasonic imaging system.

FIG. 4 shows a distal end portion of dilation catheter (112) with ultrasonic imaging system (114). Imaging dilator (118) includes an inflatable balloon body (124) similar to the balloon discussed above. Distal end portion of catheter body (122) supports balloon body (124), which is fluidly connected to fluid conduit (120) for expansion and contraction. Ultrasonic imaging system (114) further includes a plurality of electrically reactive components, such as ultrasonic transducers (126), contained within balloon body (124) of imaging dilator (118). Each ultrasonic transducer (126) is electrically connected to ultrasonic generator (116) and configured to be driven by ultrasonic generator (116) to vibrate at an ultrasonic frequency. Ultrasonic vibration of ultrasonic transducers (126) initiates a source ultrasonic signal (128) (see FIG. 5) while the fluid within balloon body (122) propagates the source ultrasonic signal (128) (see FIG. 5) radially outwardly from catheter body (122). Source ultrasonic signals (128) reflect off of anatomies engaged with balloon body (124) and return toward ultrasonic transducers (126) through the fluid as an echo ultrasonic signal (130) (see FIG. 5). Such "signals" may also be referred to herein as "waves," and it will be appreciated that such terms for "signals" and "waves" are interchangeable in the present example. One exemplary fluid is water or saline, although it will be appreciated that alternative fluids capable of propagating ultrasonic waves may be similarly used.

Ultrasonic transducers (126) positioned within balloon body (124) are also configured to receive echo ultrasonic signals (130) (see FIG. 5) for communication to a control module (132) and a display device (134) of ultrasonic imaging system (114). To this end, control module (132) receives echo ultrasonic signals (130) (see FIG. 5) as a signal data and processes the signal data to construct an image of the anatomy adjacent to balloon body (124). In the present example, the constructed image is displayed for viewing by the clinician on display device (134), such as a monitor, for providing diagnostic feedback to the clinician. By way of example, ultrasonic transducers (126) are formed of piezoelectric materials, which are configured to emit and receive ultrasonic signals as will be appreciated by one of ordinary skill in the art. Ultrasonic transducers (126) shown in FIG. 4 are arranged in a linear phased array for emitting and receiving ultrasonic signals for processing as a sonographic image shown on display device (134). Other suitable ways in which ultrasonic transducers (126) may be arranged will be apparent to those of ordinary skill in the art in view of the teachings herein.

Additionally, or alternatively, the constructed image may be analyzed by control module (132) to provide therapeutic feedback, which may be performed with dilation instrument assembly (110) by the clinician and/or directed by control module (132). In this respect, the image may not be visually rendered for viewing in some instances, but rather constructed for further processing, diagnosis, and therapeutic treatment. For example, control module (132) may direct imaging dilator (118) for automated inflation/deflation of balloon body (124) as well as direct one or more ultrasonic transducers (126) to emit ultrasonic waves for lithotripsy, deep tissue stimulation, or other ultrasonically therapeutic procedures. The invention is thus not intended to be unnecessarily limited to sonographic imaging as shown in the present example. It should also be understood that, in some versions, ultrasonic transducers (126) may be operable to vibrate in two or more different modes, including but not limited to an imaging mode and a therapeutic mode. Suitable frequencies, amplitudes, and other characteristics that may be associated with these different modes will be apparent to those of ordinary skill in the art in view of the teachings herein. As yet another merely illustrative variation, some versions may provide a first set of ultrasonic transducers (126) that are dedicated to vibrating in a first mode (e.g., an imaging mode) and a second set of ultrasonic transducers (126) that are dedicated to vibrating in a second mode (e.g., a therapeutic mode).

In use, with respect to FIGS. 2-5, dilation catheter (112) is inserted into the passageway within the patient to position balloon body (124) adjacent to a desired anatomy for dilation. For instance, the passageway may comprise a paranasal sinus ostium or other passageway associated with drainage of a paranasal sinus, a Eustachian tube, or any other suitable anatomical passageway. Balloon body (124) of dilation catheter (112) inflates with fluid via fluid conduit (120) from the contracted state shown in FIG. 3A to the expanded state shown in FIG. 3B. With respect to FIGS. 4-5, balloon body (124) is positioned within an ostium (136) and inflated to dilate the ostium as balloon body (124) engages with the surrounding anatomy.

Following inflation of balloon body (124) to the expanded state, ultrasonic generator (116) powers ultrasonic transducers (126) to ultrasonically vibrate. The ultrasonic vibrations of ultrasonic transducers (126) emit source ultrasonic signals radially outwardly from catheter body (122). Source ultrasonic signals (128) propagate through fluid and reflect inwardly from the anatomy of ostium (136) to return toward ultrasonic transducers (126) as echo ultrasonic signals (130). Ultrasonic transducers (126) receive echo ultrasonic signals (130) and communicate signal data to control module (132) for processing. Control module (132) constructs the sonographic image of the anatomy of ostium (136) and communicates the constructed sonographic image to display device (134) as a visual representation for such diagnostic and/or therapeutic effects by the clinician and described herein.

III. Dilation Catheter with a Selectively Adjustable Bend

Figure 6A:
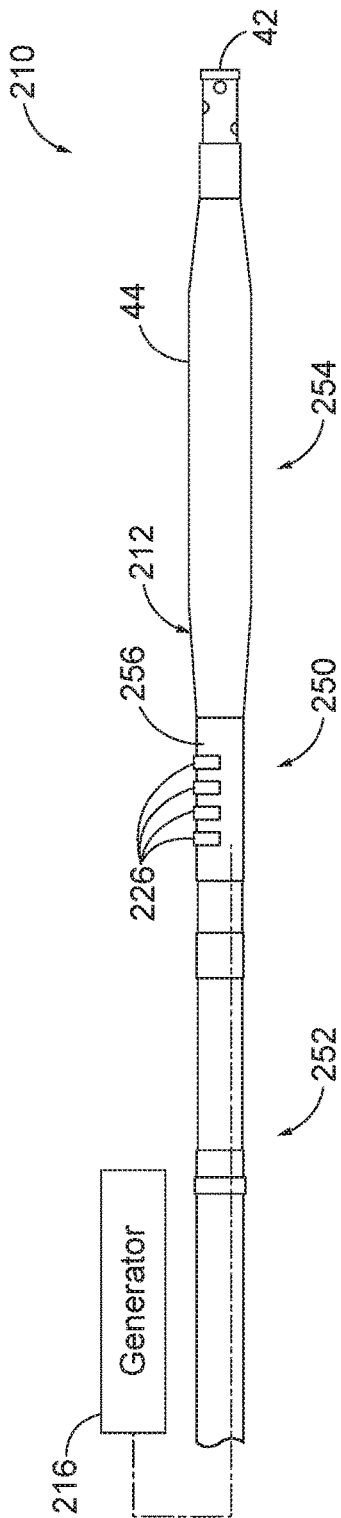
FIG. 6A depicts a side elevational view of a distal end portion of a second exemplary dilation catheter with a dilator in a contracted state and a selectively adjustable bend in a predetermined straight configuration.
Figure 6B:
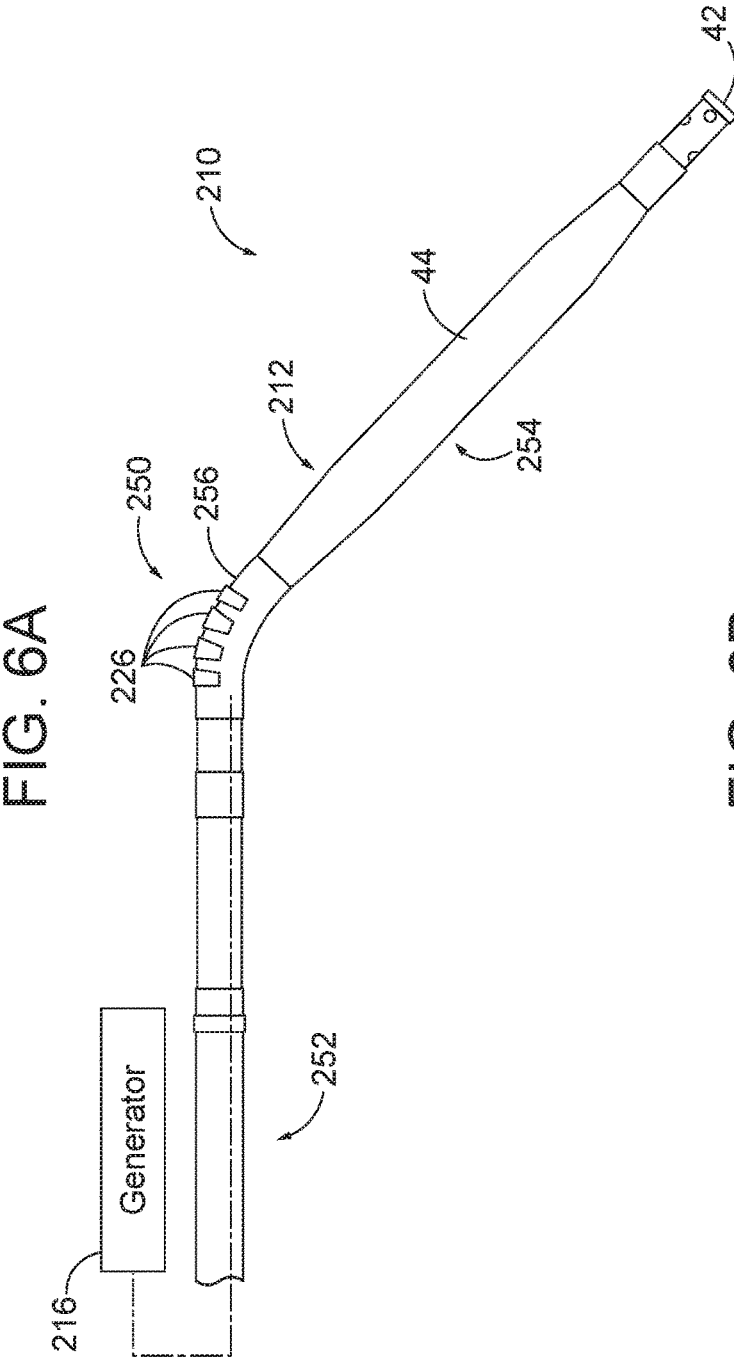
FIG. 6B depicts the side elevational view of the distal end portion of the dilation catheter similar to FIG. 6A, but with the selectively adjustable bend in a predetermined arcuate configuration.
Figure 6C:
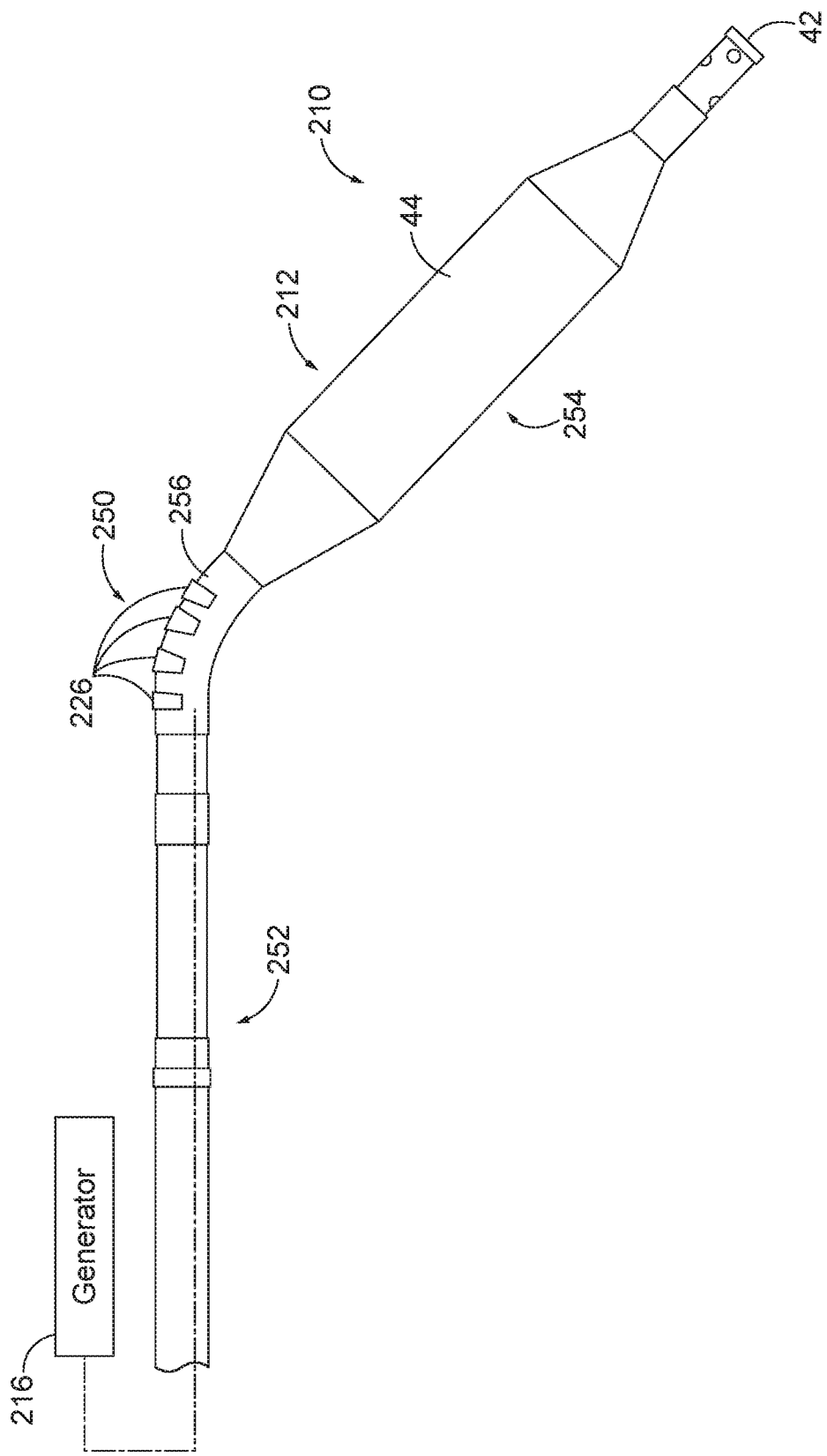
FIG. 6C depicts the side elevational view of the distal end portion of the dilation catheter similar to FIG. 6B, but with the dilator in an expanded state.

FIGS. 6A-6C show a third exemplary dilation catheter (212) for use with a dilation instrument assembly (210). Dilation catheter (212) generally operates similar to dilation catheter (40) (see FIG. 1D) with open distal end (42) and balloon (44) such that like numbers referenced below indicate like features discussed above. However, rather than a relatively uniformly constructed catheter body, such as catheter body (122) (see FIG. 2), dilation catheter (212) has a catheter body (248) with a deflectable body portion (250) connected to and extending between a proximal body portion (252) and a distal body portion (254). Dilation instrument assembly (210) further includes electrically reactive components, such as a plurality of ultrasonic transducers (226), positioned along deflectable body portion (250). Ultrasonic transducers (226) are configured to selectively expand and/or contract along deflectable body portion (250) to adjust a bend (256) of deflectable body portion (250) for repositioning balloon (44) during use.

With respect to FIG. 6A, dilation instrument assembly (210) includes a generator, such as an ultrasonic generator (216), operatively connected to each ultrasonic transducer (226). Ultrasonic generator (216) selectively powers ultrasonic transducers (226) to expand and/or contract according to one of various predetermined arrangements configured to respectively adjust bend (256) to a predetermined angle. Such ultrasonic transducers (226) are linearly arranged along deflectable body portion (250) in the present example, but may be alternatively positioned for deflecting deflectable body portion (250). Ultrasonic transducers (226) are more particularly a piezoelectrical material, but it will be appreciated that alternative materials, such as electroactive polymers, may be similarly used for selectively adjusting bend (256). In other words, some variations may use electroactive polymer elements instead of using ultrasonic transducers (226) to selectively deflect dilation catheter (212) at deflectable body portion (250). Those of ordinary skill in the art will recognize that electroactive polymers may expand or contract (and maintain an expanded or contracted state) in response to electrical energy being applied to such polymers. Various suitable materials that may be used to form such electroactive polymers will be apparent to those of ordinary skill in the art in view of the teachings herein. The invention is thus not intended to be unnecessarily limited to piezoelectrical material ultrasonic transducers (226) as shown herein.

FIG. 6B shows ultrasonic generator (216) powering ultrasonic transducers (226) to expand and/or contract in a predetermined arrangement to adjust bend (256) to the predetermined angle and thereby reposition distal body portion (254) relative to proximal body portion (252). Balloon (44), which is supported on distal body portion (254), similarly adjusts relative to proximal body portion (252) at the predetermined angle. Either before or after such repositioning, balloon (44) is inflated with fluid from the contracted state shown in FIG. 6B to the expanded state shown in FIG. 6C for dilating the anatomy. It will be appreciated that any angular bend may be achieved with the present arrangement of ultrasonic transducers (226), and the invention is not intended to be limited to the particular predetermined angle of bend (256) shown in the present example.

In some versions, ultrasonic transducers (226) (or electroactive polymers, or whatever other kind of elements are configured to laterally deflect dilation catheter (212) at deflectable body portion (250) in response to electrical energy being applied to such elements) are applied to no more than half of the angular extent of deflectable body portion (250). In other words, the electrically responsive deformation elements may extend about the circumference of deflectable body portion (250) up to only 180°. In such versions, the remaining angular extent of deflectable body portion (250) may bend laterally; yet may not be longitudinally extensible. Thus, in such versions, when electrical energy is applied to the electrically responsive deformation elements, the electrically responsive deformation elements expand longitudinally while the angularly adjacent portions of deflectable body portion (250) do not expand longitudinally, thereby resulting in lateral bending of dilation catheter (212) at deflectable body portion (250). The source of electrical power (e.g., generator (216)) may continue to apply the electrical energy to maintain the bent state of deflectable body portion (250) for as long as the operator wishes to maintain the bent state. When the operator wishes to straighten deflectable body portion, the electrical energy may be removed from the electrically responsive deformation elements, thereby allowing deflectable body portion (250) to return to a straight configuration.

As yet another merely illustrative variation, deflectable body portion (250) may comprise two or more different arrays of electrically responsive deformation elements. Such different arrays may be interposed between each other (e.g., in an alternating fashion) or otherwise arranged. Such different arrays may be electrically powered separately from each other to provide different effects. For instance, a first array of electrically responsive deformation elements may be configured to provide a first bend angle at deflectable body portion (250); while a second array of electrically responsive deformation elements may be configured to provide a second bend angle at deflectable body portion (250). In addition, or in the alternative, a set of electrically responsive elements may be configured to straighten deflectable body portion (250) and maintain a straight configuration at deflectable body portion (250) when such electrically responsive elements receive electrical power. Various suitable configurations, arrangements, and methods of operation that may be used with respect to a plurality of different arrays of electrically responsive deformation elements will be apparent to those of ordinary skill in the art in view of the teachings herein.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A dilation instrument, comprising: (a) a dilation catheter, including: (i) a catheter body configured to distally extend from an instrument body and move relative to the instrument body, (ii) a fluid conduit extending along the catheter body, (iii) a dilator connected to the catheter body and in fluid communication with the fluid conduit, wherein the dilator is configured to receive a fluid from the fluid conduit and thereby inflate from a contracted state to an expanded state, and (iv) at least one ultrasonic transducer positioned on the catheter body and configured to electrically connect to an ultrasonic generator, wherein the at least one ultrasonic transducer is configured to emit a source ultrasonic signal toward an anatomy within a patient for producing a diagnostic or a therapeutic effect.

Example 2

The dilation instrument of Example 1, wherein the at least one ultrasonic transducer comprises an array of ultrasonic transducers.

Example 3

The dilation instrument of Example 2, wherein the plurality of ultrasonic transducers includes a linear phased array of ultrasonic transducers.

Example 4

The dilation instrument of Example 3, wherein the linear phased array of ultrasonic transducers is positioned within the dilator.

Example 5

The dilation instrument of any one or more of Examples 1 through 4, wherein each of the ultrasonic transducers comprises a piezoelectric material.

Example 6

The dilation instrument of any one or more of Examples 1 through 5, further comprising an ultrasonic generator operatively connected to the at least one ultrasonic transducer.

Example 7

The dilation instrument of any one or more of Examples 1 through 6, wherein the at least one ultrasonic transducer is configured to emit the source ultrasonic signal toward an anatomy and receive an associated echo ultrasonic signal reflecting from the anatomy.

Example 8

The dilation instrument of Example 7, wherein the at least one ultrasonic transducer is positioned on the catheter body within the dilator.

Example 9

The dilation instrument of Example 8, wherein the at least one ultrasonic transducer is configured to receive the fluid thereagainst and emit the source ultrasonic signal and receive the echo ultrasonic signal through the fluid for imaging the anatomy.

Example 10

The dilation instrument of any one or more of Examples 7 through 9, further comprising a control module operatively connected to the at least one ultrasonic transducer and configured to receive data of the echo ultrasonic signal from the at least one ultrasonic transducer, wherein the control module is further configured to direct at least one of a feedback device or the dilation catheter to respond with a predetermined diagnostic communication or a predetermined therapeutic communication.

Example 11

The dilation instrument of Example 10, further comprising a feedback device operatively connected to the control module, wherein the feedback device is configured to respond with the predetermined diagnostic communication and indicate the predetermined diagnostic communication to a clinician.

Example 12

The dilation instrument of Example 11, wherein the feedback device includes a visual display and the predetermined diagnostic communication comprises an image of the anatomy within the patient, and wherein the control module and display device are collectively configured to construct the image based on the data of the echo ultrasonic signal from the at least one ultrasonic transducer.

Example 13

The dilation instrument of any one or more of Examples 1 through 12, wherein the at least one ultrasonic transducer is configured to emit the source ultrasonic signal toward the anatomy within the patient thereby therapeutically treating the anatomy.

Example 14

The dilation instrument of any one or more of Examples 1 through 13, wherein the catheter body is configured to movably receive a guidewire therein for guiding movement of the catheter body along the guidewire.

Example 15

The dilation instrument of Example 14, further comprising: (a) an instrument body; (b) a guidewire operatively connected to the instrument body and configured to move relative to the instrument body; and (c) a guide catheter configured to extend distally from the instrument body and movably receive the guidewire therein for guiding movement of the guidewire therethrough, wherein the dilation catheter is configured to translate along the guide catheter.

Example 16

A dilation instrument, comprising: (a) a dilation catheter, including: (i) a catheter body configured to distally extend from an instrument body and move relative to the instrument body and including: (A) a proximal body portion, (B) a distal body portion, and (C) a deflectable body portion extending between the proximal and distal body portion, wherein the deflectable body portion is configured to selectively deflect to reposition the distal body portion relative to the proximal body portion, (ii) an expandable dilator supported on the distal body portion, and (iii) at least one electrically reactive component positioned on the deflectable body portion of the catheter body and configured to electrically connect to an electrical power source, wherein the at least one electrically reactive component is configured to expand or contract to selectively adjust a bend of the deflectable body portion and thereby selectively reposition the expandable dilator relative to the proximal body portion for accessing an anatomy of a patient.

Example 17

The dilation instrument of Example 16, wherein the at least one electrically reactive component includes a plurality of electrically reactive components, and wherein the plurality of electrically reactive components is arranged linearly along the deflectable body portion of the catheter body.

Example 18

The dilation instrument of Example 17, wherein the plurality of electrically reactive components includes a plurality of ultrasonic transducers.

Example 19

A method of imaging an anatomy within a patient with a dilation instrument, the dilation instrument including a dilation catheter, the dilation catheter having: (i) a catheter body configured to distally extend from an instrument body and move relative to the instrument body, (ii) a fluid conduit extending along the catheter body, (iii) a dilator connected to the catheter body and in fluid communication with the fluid conduit, wherein the dilator is configured to receive a fluid from the fluid conduit and thereby inflate from a contracted state to an expanded state, and (iv) at least one ultrasonic transducer positioned on the catheter body and configured to electrically connect to an ultrasonic generator, the method comprising: (a) emitting a source ultrasonic signal from the at least one ultrasonic transducer through the fluid inflating the dilator and toward the anatomy within the patient; (b) receiving an echo ultrasonic signal in the at least one ultrasonic transducer, wherein the echo ultrasonic signal is reflected back from the anatomy in response to the source ultrasonic signal; and (c) constructing an image of the anatomy based on the echo ultrasonic signal.

Example 20

The method of Example 19, further comprising displaying the constructed image on a visual display.

V. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of imaging an anatomy within a patient with a dilation instrument, the dilation instrument including a dilation catheter, the dilation catheter having: (i) a catheter body configured to distally extend from an instrument body and move relative to the instrument body, (ii) a fluid conduit extending along the catheter body, (iii) a dilator connected to the catheter body and in fluid communication with the fluid conduit, wherein the dilator is configured to receive a fluid from the fluid conduit and thereby inflate from a contracted state to an expanded state, and (iv) at least two ultrasonic transducers positioned on the catheter body and configured to electrically connect to at least one ultrasonic generator, wherein the at least two ultrasonic transducers include a first type of ultrasonic transducer configured to produce a diagnostic effect and a second type of ultrasonic transducer configured to produce a therapeutic effect, the method comprising:
   (a) inserting the dilation catheter into an ear, nose, or throat of the patient;
   (b) communicating the fluid through the fluid conduit thereby inflating the dilator from the contracted state to the expanded state, wherein the fluid contacts the first type of ultrasonic transducer and the second type of ultrasonic transducer;
   (c) emitting a first source ultrasonic signal from the first type of ultrasonic transducer through the fluid inflating the dilator and toward the anatomy within the patient;
   (d) receiving an echo ultrasonic signal in the first type of ultrasonic transducer, wherein the echo ultrasonic signal is reflected back through the fluid within the dilator from the anatomy in response to the first source ultrasonic signal;
   (e) constructing an image of the anatomy based on the echo ultrasonic signal; and
   (f) emitting a second source ultrasonic signal from the second type of ultrasonic transducer through the fluid inflating the dilator and toward the anatomy within the patient, wherein the second source ultrasonic signal is unequal to the first source ultrasonic signal.

2. The method of claim 1, further comprising displaying the constructed image on a visual display.

3. The method of claim 1, wherein the first type of ultrasonic transducer and the second type of ultrasonic transducer are arranged into an array on the catheter body.

4. The method of claim 3, wherein the array forms a linear phased array of ultrasonic transducers.

5. The method of claim 1, wherein the first type of ultrasonic transducer and the second type of ultrasonic transducer are positioned inside the dilator.

6. The method of claim 1, further comprising:
(a) coupling the at least one ultrasonic generator with the first type of ultrasonic transducer and the second type of ultrasonic transducer; and
(b) configuring the at least one ultrasonic generator to activate the first type of ultrasonic transducer to emit the first source ultrasonic signal and the second type of ultrasonic transducer to emit the second source ultrasonic signal.

7. The method of claim 1, further comprising coupling a control module with at least one of the first type of ultrasonic transducer and the second type of ultrasonic transducer, wherein the control module receives data of the echo ultrasonic signal.

8. The method of claim 7, wherein the control module directs at least one of a feedback device or the dilation catheter to respond with a predetermined diagnostic communication or a predetermined therapeutic communication.

9. The method of claim 1, further comprising inserting a guidewire into the catheter body, wherein the guidewire guides movement of the catheter body along the guidewire.

10. The method of claim 9, further comprising coupling a guide catheter to the instrument body to thereby movably receive the guidewire therein for guiding movement of the guidewire therethrough, wherein the dilation catheter translates along the guide catheter.

11. A method of imaging an anatomy within a patient with a dilation instrument, the dilation instrument including a dilation catheter, the dilation catheter having: (i) a catheter body configured to distally extend from an instrument body and move relative to the instrument body, (ii) a fluid conduit extending along the catheter body, (iii) a dilator connected to the catheter body and in fluid communication with the fluid conduit, wherein the dilator is configured to receive a fluid from the fluid conduit and thereby inflate from a contracted state to an expanded state, and (iv) one or more ultrasonic transducers positioned on the catheter body and configured to electrically connect to at least one ultrasonic generator, wherein the one or more ultrasonic transducers are configured to selectively operate in a first mode or a second mode, the method comprising:
(a) inserting the dilation catheter into an ear, nose, or throat of a patient;
(b) communicating the fluid through the fluid conduit thereby inflating the dilator from the contracted state to the expanded state, wherein the fluid contacts the one or more ultrasonic transducers;
(c) configuring the one or more ultrasonic transducers to operate in a first mode;
(d) emitting a first source ultrasonic signal from the one or more ultrasonic transducers through the fluid inflating the dilator and toward anatomy within the head or throat of the patient;
(e) receiving an echo ultrasonic signal in the one or more ultrasonic transducers, wherein the echo ultrasonic signal is reflected back through the fluid within the dilator from the anatomy within the head or throat of the patient in response to the first source ultrasonic signal;
(f) constructing an image of the anatomy within the ear, the nose or the throat of the patient based on the echo ultrasonic signal;
(g) configuring the one or more ultrasonic transducers to operate in a second mode; and
(h) emitting a second source ultrasonic signal from the one or more ultrasonic transducers through the fluid inflating the dilator and toward the anatomy within the ear, the nose or the throat of the patient, wherein the second source ultrasonic signal is unequal to the first source ultrasonic signal.

12. The method of claim 11, wherein the first mode produces a diagnostic ultrasonic effect for the patient and the second mode produces a therapeutic ultrasonic effect for the patient.

13. The method of claim 11, wherein the one or more ultrasonic transducers is arranged into an array on the catheter body.

14. The method of claim 11, wherein the one or more ultrasonic transducers is positioned inside the dilator and within the fluid.

15. The method of claim 11, further comprising coupling a control module with at least one of the one or more ultrasonic transducers, wherein the control module receives data of the echo ultrasonic signal.

16. The method of claim 11, further comprising inserting a guidewire into the catheter body, wherein the guidewire guides movement of the catheter body along the guidewire.

17. The method of claim 16, further comprising coupling a guide catheter to the instrument body to thereby movably receive the guidewire therein for guiding movement of the guidewire therethrough, wherein the dilation catheter translates along the guide catheter.

18. A method of imaging an anatomy within a patient with a dilation instrument, the dilation instrument including a guidewire, a dilation catheter, the dilation catheter having: (i) a catheter body configured to distally extend from an instrument body and move relative to the instrument body, (ii) a fluid conduit extending along the catheter body, (iii) a dilator connected to the catheter body and in fluid communication with the fluid conduit, wherein the dilator is configured to receive a fluid from the fluid conduit and thereby inflate from a contracted state to an expanded state, and (iv) one or more ultrasonic transducers positioned on the catheter body and configured to electrically connect to at least one ultrasonic generator, wherein the one or more ultrasonic transducers are configured to selectively operate in a first mode or a second mode, the method comprising:
(a) inserting the guidewire and the dilation catheter into an ear, nose, or throat of the patient;
(b) communicating the fluid through the fluid conduit thereby inflating the dilator from the contracted state to the expanded state, wherein the fluid contacts the one or more ultrasonic transducers;
(c) emitting a first source ultrasonic signal from the one or more ultrasonic transducers through the fluid inflating the dilator and toward anatomy within the ear, the nose or the throat of the patient, wherein the first source ultrasonic signal provides a diagnostic effect;
(d) receiving an echo ultrasonic signal in the one or more ultrasonic transducers, wherein the echo ultrasonic signal is reflected back through the fluid within the dilator from the anatomy within the ear, the nose or the throat of the patient in response to the first source ultrasonic signal;
(e) receiving the data of the echo ultrasonic signal;
(f) transmitting the received data of the echo ultrasonic signal to a control module to thereby construct an image of the anatomy within the head or throat of the patient based on the echo ultrasonic signal; and
(g) emitting a second source ultrasonic signal from the one or more ultrasonic transducers through the fluid inflating the dilator and toward the anatomy within the ear, the nose or the throat of the patient, wherein the second source ultrasonic signal provides a therapeutic effect.

19. The method of claim 18, wherein a first type of ultrasonic transducer and a second type of ultrasonic transducer of the one or more ultrasonic transducers are arranged into an array on the catheter body.

20. The method of claim 18, further comprising displaying the constructed image on a visual display.

* * * * *